US010517802B2

(12) United States Patent
Siegel et al.

(10) Patent No.: US 10,517,802 B2
(45) Date of Patent: Dec. 31, 2019

(54) FRAGRANCE DISPERSION FOR DETERGENT COMPOSITIONS

(71) Applicant: Symrise AG, Holzminden (DE)

(72) Inventors: Sven Siegel, Höxter (DE); Jörg Dröge, Bodenwerder (DE); Jörn Wiedemann, Holzminden (DE); Benjamin Rost, Bodenwerder (DE)

(73) Assignee: Symrise AG, Holzminden (DE)

( * ) Notice: Subject to any disclaimer, the term of this patent is extended or adjusted under 35 U.S.C. 154(b) by 115 days.

(21) Appl. No.: 15/552,627

(22) PCT Filed: Feb. 11, 2016

(86) PCT No.: PCT/EP2016/052910
§ 371 (c)(1),
(2) Date: Aug. 22, 2017

(87) PCT Pub. No.: WO2016/134977
PCT Pub. Date: Sep. 1, 2016

(65) Prior Publication Data
US 2018/0051238 A1 Feb. 22, 2018

(30) Foreign Application Priority Data

Feb. 25, 2015 (EP) .................. 15156452.3

(51) Int. Cl.
| C11D 3/50 | (2006.01) |
| A61K 8/11 | (2006.01) |
| A61Q 13/00 | (2006.01) |
| A61K 8/04 | (2006.01) |
| C11D 3/22 | (2006.01) |
| C11D 17/00 | (2006.01) |
| A61K 8/73 | (2006.01) |
| C11D 17/06 | (2006.01) |

(52) U.S. Cl.
CPC ................ *A61K 8/11* (2013.01); *A61K 8/044* (2013.01); *A61K 8/737* (2013.01); *A61Q 13/00* (2013.01); *C11D 3/225* (2013.01); *C11D 3/50* (2013.01); *C11D 3/505* (2013.01); *C11D 17/0017* (2013.01); *C11D 17/0039* (2013.01); *C11D 17/06* (2013.01); *A61K 2800/52* (2013.01); *A61K 2800/548* (2013.01); *A61K 2800/5422* (2013.01); *A61K 2800/56* (2013.01)

(58) Field of Classification Search
CPC ....... C11D 17/0039; C11D 3/505; C11D 3/50; C11D 17/042; A61K 8/11; A61K 2800/56
See application file for complete search history.

(56) References Cited

U.S. PATENT DOCUMENTS

| 4,428,869 A | 1/1984 | Munteanu et al. |
| 2007/0111919 A1* | 5/2007 | Boerefijn ............... C11D 3/505 510/445 |
| 2011/0190191 A1* | 8/2011 | Balgobind-Narain ...................... C11D 3/505 510/349 |
| 2011/0269658 A1 | 11/2011 | Dihora et al. |
| 2014/0170194 A1* | 6/2014 | Cetti ........................ A61K 8/46 424/401 |
| 2014/0206587 A1* | 7/2014 | Chen ........................ A61K 8/66 510/119 |
| 2015/0232791 A1* | 8/2015 | Droege ................ C11D 3/1266 510/101 |
| 2016/0230128 A1* | 8/2016 | Cunningham ......... C11D 3/505 |

FOREIGN PATENT DOCUMENTS

| DE | 101 63 142 A1 | 7/2003 |
| WO | 2006/018694 A1 | 2/2006 |
| WO | 2013/026657 A1 | 2/2013 |
| WO | 2014/044461 A2 | 3/2014 |

* cited by examiner

Primary Examiner — John R Hardee
(74) Attorney, Agent, or Firm — Dilworth & Barrese, LLP

(57) ABSTRACT

The present invention belongs to the area of detergents and refers to a dispersion comprising encapsulated fragrances and the method as well as the use of the said dispersion in a process to adhere said encapsulated fragrances onto particles, powder or granules of detergent compositions.

7 Claims, No Drawings

FRAGRANCE DISPERSION FOR DETERGENT COMPOSITIONS

FIELD OF INVENTION

The present invention belongs to the area of detergents and refers to a dispersion comprising encapsulated fragrances and the method as well as the use of the said dispersion in a process to adhere said encapsulated fragrances onto particles, powder or granules of detergent compositions.

STATE OF THE ART

Fragrances are an essential constituent in laundry formulations. Thus, laundry is to have a pleasant and fresh fragrance both in the wet and in the dry state. It is therefore necessary that fragrances have good affinity for the fibres and continue to adhere thereto, in order to subsequently release the fragrances again in a retarded manner, in order that the laundry releases a pleasant fragrance note over a prolonged period. The demands on fragrances are accordingly set quite high. The basic problem in the use of fragrances is that fragrances are volatile substances. However, the effect of this property in turn is their fragrance effect. Therefore, the use of fragrances in textile and surface treatment compositions involves facing the challenge of stabilizing these volatile fragrances for long enough, such that they do not all evaporate within a very short time and do not give any fragrance effect any longer. The fragrances should evaporate off within a particular period after the cleaning and in doing so bring about a long-lasting and very homogeneous odour effect. A problem with fragrances is the fact that the fragrance impression of a perfume changes over the course of time because the odorants which constitute the fresh and light notes in the perfume evaporate off more quickly because of their high vapour pressure than the fragrances which constitute the heart and base notes. Therefore, fragrances are often encapsulated in order thus to be able to stabilize the odour impression over a prolonged period. However, this leads to the problem that the capsules comprising such fragrances, but also other ingredients customary for washing and cleaning compositions, generally after prolonged standing, sediment or rise to the top and hence destroy the stability of the laundry formulation.

WO 2014/016395 A1 relates to microcapsules having particle size distributions that has at least two maxima, wherein the main maximum of the particle size lies in the range of 5 to 100 μm and wherein the volume assumed by the microcapsules that have a particle size less than ¼ of the particle size of the main maximum is greater than approximately 20% of the total volume of the microcapsules. A particularly suitable form of the use of the microcapsules consists of admixing it with the end product in the form of a suspension, which is in particular in water. In order to prevent mixing of said suspension and to achieve high storage stability, the suspension should have a viscosity of 12 to 1500 mPas, which is obtained through the employment of a thickening agent.

The incorporation of perfumes or fragrances into washing and cleaning compositions, especially laundry compositions can lead to problems. For example, incompatibilities between the individual active ingredient components, e.g. perfumes or fragrances with bleaches, enzymes, dyes, etc. of the washing and cleaning compositions can occur. This can lead to unwanted discolouration, agglomeration, odour problems and breakdown of washing-active ingredients. However, the consumer expects washing and cleaning compositions which display optimal action at the time of the use even after storage and transport. This means that the ingredients of the washing and cleaning composition have not settled out, broken down or evaporated off beforehand.

The problems addressed to the present invention was to improve the manufacture process of detergent compositions which consists of particles, powder or granules, especially in the following aspects:
decreasing clumping and improving the flowability of the particles, powder or granules;
reducing production disruptions,
improving the product throughput rate,
and in particular in the step of perfuming said particles, powder or granules of detergent compositions the following aspects have been aimed to be improved:
reduced capsule disruptions,
homogeneous distribution of the fragrances onto the detergent particles, powder or granules,
reducing loss of fragrances in the process steps,
improving storage stability and handling of the fragrance formulation in the manufacture process.

The problems can be solved by the dispersion of the present invention as described herein.

DESCRIPTION OF THE INVENTION

Object of the present invention is a dispersion, comprising
A) 0.1 wt. % to 80 wt. %, preferably 1 wt. % to 70 wt. %, more preferred 15 wt. % to 50 wt. % encapsulated fragrances;
B) optionally 0.001 wt. % to 10 wt. %, preferably 0.01 wt. % to 7 wt. %, more preferred 0.01 wt. % to 2 wt. % viscosity modifiers,
C) optionally 0.001 wt. % to 80 wt. %, preferably 0.1 wt. % to 70 wt. %, more preferred 15 wt. % to 50 wt. % non-encapsulated fragrances,
D) 0.001 wt. % to 99 wt. % additives,
E) 30 wt. % to 99 wt. %, preferably 40 wt. % to 98 wt. %, more preferred 50 wt. % to 95 wt. % water;
all weight percent of the compounds A) to E) are referred to the total amount of the dispersion and with the proviso that the components add to 100 wt. %.

In a preferred embodiment the dispersion of the present invention comprises:
A) 10 wt. % to 60 wt. % encapsulated fragrances,
B) 0.01 wt. % to 5 wt. % viscosity modifiers,
C) optionally 0.001 wt. % to 80 wt. % non-encapsulated fragrances,
D) 0.001 wt. % to 99 wt. % additives,
E) 30 wt. % to 99 wt. % water,
all weight percent of the compounds A) to E) are referred to the total amount of the dispersion and with the proviso that the components add to 100 wt. %.

In another preferred embodiment the dispersion of the present invention comprises:
A) 20 wt. % to 40 wt. % encapsulated fragrances,
B) 0.01 wt. % to 2 wt. % viscosity modifiers,
C) optionally 0.001 wt. % to 80 wt. % non-encapsulated fragrances,
D) 0.001 wt. % to 99 wt. % additives,
E) 50% to 99 wt. % water,
all weight percent of the compounds A) to E) are referred to the total amount of the dispersion and with the proviso that the components add to 100 wt. %.

Preferably, the dispersion of the present invention shows the advantage of a thixotropic rheological character and is stable during storage and handling in the further manufacture process. Further, the dispersion of the present invention shows benefits in the manufacture process of perfumed detergent compositions, which consists in particular of particles, powder or granules.

Also advantageously, the encapsulated fragrances can be dispersed in a stable manner in the aqueous medium of the present invention. "Stable" means that the compositions are stable at room temperature and 40° C. over a period of at least 4 weeks and preferably of at least 6 weeks, without creaming or sedimentation of the compositions.

Suitable viscosity modifiers for the dispersion of the present invention are selected from the group consisting of water soluble polymers such as polyvinyl pyrrolidone, water soluble cellulose; polyvinyl alcohol; ethylene maleic anhydride copolymer; methyl vinyl ether maleic anhydride copolymer; polyethylene oxides; water soluble polyamide or polyester; copolymers or homopolymers of acrylic acid such as polyacrylic acid, polystyrene acrylic acid copolymers or mixtures of two or more of these. Examples of suitable water-soluble hydroxyalkyl and carboxyalkyl celluloses include hydroxyethyl and carboxymethyl cellulose, hydroxymethyl and carboxymethyl cellulose, hydroxypropyl carboxymethyl cellulose, hydroxypropyl methyl carboxyethyl cellulose, hydroxypropyl carboxypropyl cellulose, hydroxybutyl carboxymethyl cellulose and the like. Also useful are alkali metal salts of these carboxy alkyl celluloses, particularly and preferably the sodium and potassium derivative and mixtures thereof.

Further useful viscosity modifiers can comprise, for example, a polyacrylates, xanthan gum, gellan gum, guar seed flour, alginate, carrageenan, bentonite, wellan gum, carob seed flour, agar agar, tragacanth, gum arabic, pectins, polyoses, starch, dextrins, gelatine and casein.

The polyacrylic and polymethacrylic viscosity modifiers include, for example, the high molecular weight homopolymers of acrylic acid crosslinked with a polyalkenyl polyether, in particular an allyl ether of sucrose, pentaerythritol or propylene (INCI name according to "International Dictionary of Cosmetic Ingredients" of The Cosmetic, Toiletry and Fragrance Association (CTFA): Carbomer), which are also referred to as carboxyvinyl polymers. Such polyacrylic acids are available inter alia from 3V Sigma under the trade name Polygel®, e.g. Polygel DA, and from B.F. Goodrich under the trade name Carbopol®, e.g. Carbopol 940 (molecular weight about 4 000 000), Carbopol 941 (molecular weight about 1 250 000) or Carbopol 934 (molecular weight about 3 000 000). Furthermore, these include the following acrylic acid copolymers: (i) copolymers of two or more monomers from the group of acrylic acid, methacrylic acid and its simple esters formed preferably with C1-4-alkanols (INCI Acrylates Copolymer), which include for example the copolymers of methacrylic acid, butyl acrylate and methyl methacrylate (CAS name according to Chemical Abstracts Service: 25035-69-2) or of butyl acrylate and methyl methacrylate (CAS 25852-37-3) and which are available for example by Rohm and Haas under the trade names Aculyn® and Acusol®, and also by Degussa (Goldschmidt) under the trade name Tego® Polymer, e.g. the anionic nonassociative polymers Aculyn 22, Aculyn 28, Aculyn 33 (crosslinked), Acusol 810, Acusol 820, Acusol 823 and Acusol 830 (CAS 25852-37-3); (ii) crosslinked high molecular weight acrylic acid copolymers, which include for example the copolymers, crosslinked with an allyl ether of sucrose or of pentaerythritol, of C10-30-alkyl acrylates with one or more monomers from the group of acrylic acid, methacrylic acid and their simple esters, formed preferably with C1-4-alkanols (INCI Acrylates/C10-30 Alkyl Acrylate Crosspolymer) and which are available for example from B.F. Goodrich under the trade name Carbopol®, e.g. the hydrophobicized Carbopol ETD 2623 and Carbopol 1382 (INCI Acrylates/C10-30 Alkyl Acrylate Crosspolymer), and Carbopol Aqua 30 (formerly Carbopol EX 473).

A further polymeric viscosity modifier to be used with preference is xanthan gum, a microbial anionic heteropolysaccharide which is produced from *Xanthomonas campestris* and a few other species under aerobic conditions and has a molar mass of from 2 to 15 million Daltons. Xanthan is formed from a chain with beta-1,4-bonded glucose (cellulose) with side chains. The structure of the subgroups consists of glucose, mannose, glucuronic acid, acetate and pyruvate, where the number of pyruvate units determines the viscosity of the xanthan gum. Suitable viscosity modifiers are in particular also a fatty alcohol. Fatty alcohols can be branched or unbranched and of native origin or petrochemical origin. Preferred fatty alcohols have a carbon chain length of from 10 to 20 carbon atoms, preferably 12 to 18. Preference is given to using mixtures of different carbon chain lengths, such as tallow fatty alcohol or coconut fatty alcohol. Examples are Lorol® Spezial (C12-14-ROH) or Lorol® Technisch (C12 18-ROH) (both from Cognis).

Preferred viscosity modifiers are herein in particular guar-2-hydroxypropylether, xanthan gum, gellan gum and polyacrylic acid or derivatives thereof and mixtures thereof.

It has been shown that the viscosity modifiers using to form the dispersion of the present invention are especially suitable in order to influence the viscosity of the dispersion in thus a way that gives more control in aspects of the manufacture process of the end product, which is in particular a perfumed detergent composition. The amount of the viscosity modifier used here is therefore dependent on the type of viscosity modifiers and the desired degree of viscosity, but is advantageously in an amount from 0.001 wt. % to 10 wt. %, preferably 0.01 wt. % to 7 wt. %, more preferred 0.01 wt. % to 2 wt. % for the dispersion of the present invention.

Suitable additives (compound D) are emulsifiers, stabilizers, anionic, nonionic, cationic, amphoteric or zwitterionic (co-)surfactants, organic solvents, builders, enzymes and additional auxiliaries such as soil repellents, thickeners, colorants optical brighteners, complexing agents, bleaches, bleach activators, dyes, antioxidants, active antimicrobial ingredients, greying inhibitors, anti-redisposition agents, pH modifiers, electrolytes, foam inhibitors and UV absorbers, preservatives, pearlescent agents and the like.

The ratio between the components (A+B+E):C in a dispersion of the present invention is preferably in the range from 1:10 to 2:1, preferably in the range from 1:8 to 1:1. A range of 1:8 means that more non-encapsulated fragrances is present than encapsulated fragrances in the capsule slurry.

The dispersion of the present invention preferably possess about 40% capsules, which means that the dispersion contains about 30% fragrances and about 10% carrier materials, in case of 35% capsules then contains 25% fragrances and 10% carrier materials.

The ratio between compound (A+B+E):D is typically preferably in the range from 9:1 to 19:1.

In a preferred embodiment the viscosity of the dispersion of the present invention is preferably from 5 mPas to 400 mPas, preferred from 15 mPas to 300 mPas, more preferred 20 mPas to 250 mPas.

Dispersions with lower viscosity, preferably lower than 5 mPas tend to undergo separation, whereas dispersion with high viscosity, preferably higher than 400 mPas are difficult to spray, which is not advantageously for the further manufacture process of perfumed detergent compositions. Ideally, dispersions of the present invention within the said viscosity ranges show a rheological behavior which has a thixotropic character and thus the fragrance capsules are held in suspense. Further, preferably the dispersions of the present invention keep their thixotropic features at low(er) shear strength.

The homogeneous distribution of encapsulated fragrances in the dispersion of the present invention allows a constant concentration of fragrances when spraying the dispersion onto particles, powder or granules of detergent compositions, and thus a homogeneous distribution of fragrances onto the detergent particles, powder or granules.

The dispersion of the present invention allows the control of the dispersion's viscosity, and thus more control over the manufacture steps in which there is a spraying step of said dispersions.

A further aspect of the present invention is the use of the dispersion according to the present invention in a process to produce perfumed particles, powder or granules. The particles, powder or granules are characterized in that the non-encapsulated and/or encapsulated fragrances of the dispersion are thus anchored to individual particles, or granules of a composition. Preferably, said particles, powder or granules, are used in washing or cleaning compositions, and preferably are used in detergent compositions. Preferably the viscosity of the used dispersion in the process is from 5 mPas to 400 mPas.

In a further embodiment the viscosity of the dispersion of the present invention
(a) decreases at higher shearing stress and
(b) increases at lower shear stress.

The viscosity is preferably in the range from 0.1 Pas to 0.75 Pas, while the shearing stress is in the range from 2.5 tau to 16 tau. Whereas when the shearing stress is lower than 2.5 tau the viscosity is preferably in the range from 0.75 Pas to 3.5 Pas.

In a further embodiment the capsules of the encapsulated fragrances in the dispersion of the present invention have a $d_v(50)$ value from 5 µm to 60 µm, preferably from 10 µm to 50 µm, more preferred from 10 µm to 40 µm and/or a $d_v(90)$ value from 140 µm to 180 µm, preferably 145 µm to 170 µm, more preferably from 150 µm to 160 µm.

Surprisingly, it has been observed that the dispersion of the present invention serve all the below mentioned needs simultaneously in a manufacture process and thus are advantage for the production of particulate washing and cleaning compositions, preferably particulate detergent compositions:
  reducing disruption in the production process,
  avoiding the degradation of sensitive detergent ingredients, such as enzymes, dyes etc.,
  decreasing the clumping and improving flowability of the particles, powders or granules (of the end-product);
  uniform distribution of the fragrance capsules onto the particles, powders or granules of the laundry composition,
  decreasing the ratio of capsule rupture during the process of the laundry particles, powder or granules,
  providing a high product throughput rate.

Therefore, a further aspect of the present invention is the use of the dispersion of the present invention
a) for improving homogenous distribution of encapsulated fragrances when spraying the said dispersion onto particles, powder or granules of a composition, which are preferably particles, powder or granules of a detergent composition, and/or
b) for reducing capsule disruption (of the encapsulated fragrances) during the production of perfumed particles, powders or granules of a detergent composition, and/or
c) or enhancing the loading of (encapsulated and/or non-encapsulated) fragrances onto the particles, powder or granules of a detergent composition.

Suitable fragrances in the sense of the present invention are described in the following and may be used in encapsulated form, but also in non-encapsulated form.

Fragrances

Fragrances or perfume oils which are used with preference in the washing and cleaning compositions, preferably laundry compositions, can be encapsulated or as so called non-encapsulated fragrances and are not subject to any restrictions at all. For instance, fragrances used may be individual odourant compounds, both synthetic and natural compounds of the ester, ether, aldehyde, ketone, alcohol, hydrocarbon, acid, carboxylic ester, aromatic hydrocarbon, aliphatic hydrocarbon, saturated and/or unsaturated hydrocarbon type, and mixtures thereof. Fragrance aldehydes or fragrance ketones used may be all the customary fragrance aldehydes and fragrance ketones which are typically used to bring about a pleasant fragrance sensation. Suitable fragrance aldehydes and fragrance ketones are common knowledge to those skilled in the art. Fragrance ketones may include all ketones which can impart a desirable fragrance or a sensation of freshness. It is also possible to use mixtures of different ketones. For example, the ketone may be selected from the group consisting of buccoxime, isojasmone, methyl beta-naphthyl ketone, musk indanone, Tonalid/musk plus, alpha-damascone, beta-damascone, delta-damascone, isodamascone, damascenone, damarose, methyl dihydrojasmonate, menthone, carvone, camphor, fenchone, alpha-ionone, beta-ionone, dihydro-beta-ionone, gamma-methylionone (so-called), fleuramone, dihydrojasmone, cisjasmone, Iso-E-Super, methyl cedrenyl ketone or methyl-cedrylone, acetophenone, methylacetophenone, para-methoxyacetophenone, methyl beta-naphthyl ketone, benzylacetone, benzophenone, para-hydroxyphenylbutanone, celery ketone or livescone, 6-isopropyldecahydro-2-naphthone, dimethyloctenone, Freskomenthe, 4 (1-ethoxyvinyl)-3,3,5,5-tetramethylcyclohexanone, methylheptenone, 2-(2-(4-methyl-3-cyclohexen-1-yl)propyl)cyclopentanone, 1-(p-menthen-6(2)-yl)-1-propa none, 4-(4-hydroxy-3-methoxyphenyl)-2-buta none, 2-acetyl-3,3-dimethylnorbornane, 6,7-dihydro-1,1,2,3,3-pentamethyl-4 (5H)-indanone, 4-damascol, dulcinyl or cassione, gelsone, hexalone, isocyclemone E, methyl-cyclocitrone, methyl-lavender ketone, orivone, para-tertbutylcyclohexanone, verdone, delphone, muscone, neobutenone, plicatone, veloutone, 2,4,4,7-tetramethyloct-6-en-3-one, tetramerane, hedione and mixtures thereof. The ketones may preferably be selected from alpha-damascone, delta-damascone, isodamascone, carvone, gamma-methylionone, Iso-E-Super, 2,4,4,7-tetramethyloct-6-en-3-one, benzylacetone, beta-damascone, damascenone, methyl dihydrojasmonate, methylcedrylone, hedione and mixtures thereof.

Suitable fragrance aldehydes may be any desired aldehydes which, in the same way as for the fragrance ketones, impart a desired odour or a sensation of freshness. Again they may be individual aldehydes or aldehyde mixtures. Suitable aldehydes are, for example, melonal, triplal, ligustral, adoxal, anisaldehyde, cymal, ethylvanillin, florhydral, floralozone, helional, heliotropin, hydroxycitronellal, koavone, lauryl aldehyde, canthoxal, lyral, lilial, adoxal, anisaldehyde, cumal methylnonylacetaldehyde, citronellal, citronellyloxyacetaldehyde, cyclamen aldehyde, bourgeonal, p,t-bucinal, phenylacetaldehyde, undecylenealdehyde, vanillin; 2,6,10-trimethyl-9-undecenal, 3-dodecen-1-al, alpha-n-amylcinnamaldehyde, 4-methoxybenzaldehyde, benzaldehyde, 3-(4-tert-butylphenyl)propanal, 2-methyl-3-(para-methoxyphenyl)propanal, 2-methyl-4-(2,6,6-trimethyl-2(1)-cyclohexen-1-yl)butanal, 3-phenyl-2-propenal, cis/trans-3,7-dimethyl-2,6-octadien-1-al, 3,7-dimethyl-6-octen-1-al, [(3,7-dimethyl-6-octenyl)oxy]acetaldehyde, 4 isopropylbenzyl aldehyde, 1,2,3,4,5,6,7,8-octahydro-8,8-dimethyl-2-naphthaldehyde, 2,4-dimethyl-3-cyclohexene-1-carboxyaldehyde, 2-methyl-3-(isopropylphenyl)propanal, decyl aldehyde, 2,6-dimethyl-5-heptenal; 4-(tricyclo[5.2.1.0(2,6)] decylidene-8)-butanal; octahydro-4,7-methano-1H-indenecarboxaldehyde; 3-ethoxy-4-hydroxybenzaldehyde, para-ethyl-alpha,alpha-dimethylhydrocinnamaldehyde, alpha-methyl-3,4-(methylenedioxy)hydrocinnamaldehyde, 3,4-methylenedioxybenzaldehyde, alpha-n-hexylcinnamaldehyde, m-cymene-7-carboxaldehyde, alpha-methylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexenecarboxaldehyde, 1-dodecanal, 2,4-dimethylcyclohexene-3-carboxaldehyde, 4-(4-hydroxy-4-methylpentyl)-3-cyclohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert-butyl)propanal, 3-(4-ethylphenyl)-2,2-dimethylpropanal, 3-(4-methoxyphenyl)-2-methylpropanal, methylnonylacetaldehyde, 2 phenylpropan-1-al, 3-phenylprop-2-en-1-al, 3-phenyl-2-pentylprop-2-en-1-al, 3-phenyl-2-hexylprop-2-enal, 3-(4-isopropylphenyl)-2-methylpropan-1-al, 3-(4-ethylphenyl)-2,2-dimethylpropan-1-al, 3-(4-tert-butylphenyl)-2-methylpropanal, 3-(3,4-methylenedioxyphenyl)-2-methylpropan-1-al, 3-(4-ethylphenyl)-2,2-dimethylpropanal, 3-(3-isopropylphenyl)butan-1-al, 2,6-dimethylhept-5-en-1-al, dihydrocinnamaldehyde, 1-methyl-4-(4-methyl-3-pentenyl)-3-cyclohexene-1-carboxaldehyde, 5- or 6-methoxyhexahydro-4,7-methanoindane-1- or -2-carboxyaldehyde, 3,7-dimethyloctan-1-al, 1-undecanal, 10-undecen-1-al, 4-hydroxy-3-methoxybenzaldehyde, 1-methyl-3-(4-methylpentyl)-3-cyclohexenecarboxyaldehyde, 7 hydroxy-3,7-dimethyloctanal; trans-4-decenal, 2,6-nonadienal, para-tolylacetaldehyde; 4 methylphenylacetaldehyde, 2-methyl-4-(2,6,6-trimethyl-1-cyclohexen-1-yl)-2-butenal, ortho-methoxycinnamaldehyde, 3,5,6-trimethyl-3-cyclohexenecarboxaldehyde, 3,7-dimethyl-2-methylene-6-octenal, phenoxyacetaldehyde; 5,9-dimethyl-4,8-decadienal, peony aldehyde (6,10-dimethyl-3-oxa-5,9-undecadien-1-al), hexahydro-4,7-methanoindane-1-carboxaldehyde, octanal, 2-methyloctanal, alpha-methyl-4-(1-methylethyl)benzeneacetaldehyde, 6,6-dimethyl-2-norpinene-2-propionaldehyde, para-methylphenoxyacetaldehyde, 2-methyl-3-phenyl-2-propen-1-al, 3,5,5-trimethylhexanal, hexahydro-8,8-dimethyl-2-naphthaldehyde, 3-propylbicyclo[2.2.1]hept-5-ene-2-carbaldehyde, 9-decenal, 3-methyl-5-phenyl-1-pentanal, methylnonylacetaldehyde, 1-p-menthene-q-carboxaldehyde, citral or mixtures thereof, lilial citral, 1-decanal, n-undecanal, n-dodecanal, florhydral, 2,4-dimethyl-3-cyclohexene-1-carboxaldehyde, 4-methoxybenzaldehyde, 3-methoxy-4-hydroxybenzaldehyde, 3-ethoxy-4-hydroxybenzaldehyde, 3,4-methylenedioxybenzaldehyde and 3,4-dimethoxybenzaldehyde and mixtures thereof. As observed by way of example above, the fragrance aldehydes and fragrance ketones may have an aliphatic, cycloaliphatic, aromatic, ethylenically unsaturated structure or a combination of these structures. There may also be further heteroatoms or polycyclic structures present. The structures may have suitable substituents such as hydroxyl groups or amino groups. For further suitable fragrances, selected from aldehydes and ketones, reference is made to Steffen Arctander, published 1960 and 1969 respectively, reprinted 2000 ISBN: Aroma Chemicals Vol. 1: 0-931710-37-5, Aroma Chemicals Vol. 2: 0-931710-38-3.

Suitable odourant compounds of the ester type are, for example, benzyl acetate, phenoxyethyl isobutyrate, p-tert-butylcyclohexyl acetate, linalyl acetate, dimethylbenzyl carbinyl acetate (DMBCA), phenylethyl acetate, benzyl acetate, ethyl methyl phenylglycinate, allyl cyclohexylpropionate, styrallyl propionate, benzyl salicylate, cyclohexyl salicylate, floramate, melusate and jasmacyclate. Odourant compounds of the hydrocarbon type are, for example, terpenes such as limonene and pinene. Suitable fragrances of the ether type are, for example, benzyl ethyl ether and ambroxane. Suitable fragrance alcohols are, for example, 10-undecen-1-ol, 2,6-dimethylheptan-2-ol, 2-methylbutanol, 2-methylpentanol, 2-phenoxyethanol, 2-phenylpropanol, 2-tert-butylcyclohexanol, 3,5,5-trimethylcyclohexanol, 3-hexanol, 3-methyl-5-phenylpentanol, 3-octanol, 1-octen-3-ol, 3-phenylpropanol, 4-heptenol, 4-isopropylcyclohexanol, 4-tert-butylcyclohexanol, 6,8-dimethyl-2-nonanol, 6-nonen-1-ol, 9-decen-1-ol, alpha-methylbenzyl alcohol, alpha-terpineol, amyl salicylate, benzyl alcohol, benzyl salicylate, beta-terpineol, butyl salicylate, citronellol, cyclohexyl salicylate, decanol, dihydromyrcenol, dimethylbenzyl carbinol, dimethylheptanol, dimethyloctanol, ethyl salicylate, ethylvanillin, anethol, eugenol, geraniol, heptanol, hexyl salicylate, isoborneol, isoeugenol, isopulegol, linalool, menthol, myrtenol, n-hexanol, nerol, nonanol, octanol, para-menthan-7-ol, phenylethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, and cinnamyl alcohol; if two or more fragrance alcohols are present, they may be selected independently of one another.

Fragrances and perfume oils may also be natural odourant mixtures, such as those obtainable from plant sources, examples being pine, citrus, jasmine, patchouli, rose or ylang-ylang oil. Likewise suitable are clary sage oil, camomile oil, clove oil, balm oil, mint oil, cinnamon leaf oil, lime blossom oil, juniper berry oil, vetiver oil, olibanum oil, galbanum oil and labdanum oil, and also orange blossom oil, neroli oil, orange peel oil and sandalwood oil. Essential oils such as angelica root oil, aniseed oil, arnica blossom oil, basil oil, bay oil, champaca flower oil, silver fir oil, silver fir cone oil, elemi oil, eucalyptus oil, fennel oil, pine needle oil, galbanum oil, geranium oil, gingergrass oil, guaiac wood oil, gurjan balsam oil, helichrysum oil, ho oil, ginger oil, iris oil, cajeput oil, sweet flag oil, camomile oil, camphor oil, cananga oil, cardamom oil, cassia oil, pine needle oil, copaiba balsam oil, coriander oil, spearmint oil, caraway oil, cumin oil, lavender oil, lemongrass oil, lime oil, mandarin oil, melissa oil, amber seed oil, myrrh oil, clove oil, neroli oil, niaouli oil, olibanum oil, oregano oil, palmarosa oil, patchouli oil, peru balsam oil, petitgrain oil, pepper oil, peppermint oil, pimento oil, pine oil, rose oil, rosemary oil, sandalwood oil, celery oil, spike oil, star anise oil, turpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronella oil, citrus oil and cypress oil.

Likewise suitable as fragrances are what are called fragrance precursors (pro-drugs). This class of compounds comprises compounds which release a desired odour molecule and/or fragrance molecule through the breaking of a chemical bond, by hydrolysis, for example. To form a fragrance precursor, typically, a desired fragrance raw material is joined chemically to a carrier, preferably a carrier of low or moderate volatility. The combination results in a less volatile and more strongly hydrophobic fragrance precursor, with better attachment to materials. The fragrance is released subsequently by breaking of the bond between the fragrance raw material and the carrier, as a result of a change in pH, for example (through perspiration during wear, for example), atmospheric humidity, heat and/or sunlight during storage or during drying on a washing line.

The fragrance raw material for use in fragrance precursors typically comprises saturated or unsaturated volatile compounds containing an alcohol, an aldehyde and/or a ketone group. The fragrance raw materials that are useful herein include any pleasingly odourous substances or mixtures of substances which have already been described above.

Particularly advantageous fragrance precursors which can be used conform to the formula (III)

R—C(OR1)(OR2)-OR3    (III)

in which R is hydrogen, linear C1-C8 alkyl, branched C3-C20 alkyl, cyclic C3-C20 alkyl, branched cyclic C6-C20 alkyl, linear C6-C20 alkenyl, branched C6-C20 alkenyl, cyclic C6-C20 alkenyl, branched cyclic C6-C20 alkenyl, substituted or unsubstituted C6-C20 aryl and mixtures thereof; R1, R2 and R3 independently are linear, branched or substituted C1-C20 alkyl; linear, branched or substituted C2-C20 alkenyl; substituted or unsubstituted, cyclic C3-C20 alkyl; substituted or unsubstituted C6-C20 aryl, substituted or unsubstituted C2-C40 alkyleneoxy; substituted or unsubstituted C3-C40 alkyleneoxyalkyl; substituted or unsubstituted C6-C40 alkylenearyl; substituted or unsubstituted C6-C32 aryloxy; substituted or unsubstituted C6-C40 alkyleneoxyaryl; C6-C40 oxyalkylenearyl and mixtures thereof.

Further particularly advantageous fragrance precursors which can be used are acetals or ketals, preferably conforming to the formula (IV)

R—C(R1)(OR3)-OR2    (IV)

in which R is linear C1-C20 alkyl, branched C3-C20 alkyl, cyclic C6-C20 alkyl, branched cyclic C6-C20 alkyl, linear C2-C20 alkenyl, branched C3-C20 alkenyl, cyclic C6-C20 alkenyl, branched cyclic C6-C20 alkenyl, substituted or unsubstituted C6-C20 aryl and mixtures thereof; R1 is hydrogen or R; R2 and R3 are each independently selected from the group consisting of linear C1-C20 alkyl, branched C3-C20 alkyl, cyclic C3-C20 alkyl, branched cyclic C6-C20 alkyl, linear C6-C20 alkenyl, branched C6-C20 alkenyl, cyclic C6-C20 alkenyl, branched cyclic C6-C20 alkenyl, C6-C20 aryl, substituted C7-C20 aryl and mixtures thereof. The use of such substances, especially in (preferably water-insoluble) microcapsules, corresponds to one preferred embodiment of the invention.

Further particularly advantageous fragrance precursors which can be used conform to the formula (V)

R4O—C(OR1)(OR3)-OR2    (V)

in which R1, R2, R3 and R4 are each independently linear, branched or substituted C1-C20 alkyl; linear, branched or substituted C2-C20 alkenyl; substituted or unsubstituted, cyclic C5-C20 alkyl; substituted or unsubstituted C6-C20 aryl, substituted or unsubstituted C2-C40 alkyleneoxy; substituted or unsubstituted C3-C40 alkyleneoxyalkyl; substituted or unsubstituted C6-C40 alkylenearyl; substituted or unsubstituted C6-C32 aryloxy; substituted or unsubstituted C6-C40 alkyleneoxyaryl; C6-C40 oxyalkylenearyl; and mixtures thereof. The use of such substances, especially in (preferably water-insoluble) microcapsules, corresponds to one preferred embodiment of the invention.

It is particularly preferable for the odourants used to comprise silicic ester mixtures. Silicic esters are described for example by the formula (VI)

R—(—O—Si(OR)2-)n-OR    (VI)

where each R is independently selected from the group containing H, the straight-chain or branched, saturated or unsaturated, substituted or unsubstituted C1-C6 hydrocarbon radicals and the fragrance alcohol radicals and/or biocide alcohol radicals, and m adopts values from the range from 1 to 20 and n adopts values from the range from 2 to 100. The silicic esters of the formula (VI) preferably comprise at least one fragrance alcohol radical and/or biocide alcohol radical.

The effect of the presence of silicic ester mixtures is often that the fragrance impression achievable, both with regard to pleasance and intensity, can be improved still further. The fragrance impression is not just qualitatively better, i.e. with regard to pleasance, but also lasts longer.

The silicic ester mixtures may also be present in the microcapsules. If the silicic ester mixtures in the microcapsules make up preferably at least 2% by weight of the total amount of encapsulated odourant, this is a preferred embodiment of the invention, which brings about a further improvement in the desired pleasing odour effect after drying.

Particularly suitable fragrance precursors are reaction products of compounds comprising at least one primary and/or secondary amine group, for example an amino-functional polymer, especially an amino-functional silicone, and a fragrance constituent selected from ketone, aldehyde and mixtures thereof. The use of such substances, especially in (preferably water-insoluble) microcapsules, corresponds to a preferred embodiment of the invention.

The total amount of (encapsulated and/or non-encapsulated) fragrances used in the final compositions, which are herein washing and cleaning compositions, preferably detergent compositions is preferably from 0.01% to 5% by weight, more preferably from 0.1% to 3% by weight and most preferably from 0.5% to 2% by weight, based on the total amount of the composition.

The term "encapsulated fragrances" means that the fragrances or a mixture of fragrances for use in the dispersion in the sense of the present invention is encased in or as if in a capsule. "Non-encapsulated fragrances" in terms of the present invention are "free" fragrances or mixture of "free" fragrances, that can be added additionally to the dispersion of the present invention, and which are not encased in or as if in a capsule.

Preference is given to using mixtures of different fragrances (from the different fragrance classes mentioned above) which together produce a pleasing fragrance note. In this case, the total amount of the at least one fragrance is the amount of all the fragrances in the mixture together, based on the total amount of the composition.

Usually the ratio of encapsulated fragrances to non-encapsulated fragrances are from 1:10 to 2:1, preferably from 1:8 to 1:1.

This ratio between encapsulated and non-encapsulated fragrances contributes to the homogeneous distribution of fragrances in the present dispersion and thus results in a homogeneous spraying of fragrances onto particles, powder or granule of the washing or cleaning compositions, preferably detergent compositions. Further, spraying such a dispersion of the present invention, which exhibits that kind of ratio between encapsulated and non-encapsulated fragrances leads to a high loading of fragrances onto particles, powder or granules of the washing or cleaning composition, preferably laundry composition.

Capsules

The capsule materials using to form encapsulated fragrances, but also used to form the particles, powder or granules of the washing and cleaning compositions, preferably the detergent compositions of the present invention may be particles, microcapsules or speckles, but also granules, compounds and fragrance beads, preference being given to microcapsules.

The term "microcapsules" is understood to mean aggregates containing at least one solid or liquid core surrounded by at least one continuous shell, especially a shell of polymer(s). Typically, these are finely dispersed liquid or solid phases coated with film-forming polymers, the production of which involves precipitating the polymers, after emulsification and coacervation or interfacial polymerization, on the material to be coated. The microscopically small capsules can be dried like powders. Also known in addition to single-core microcapsules are multi-core aggregates, also called microspheres, which contain two or more cores distributed in the continuous shell material. Single- or multicore capsules may additionally be encased by an additional second, third, etc. shell. Preference is given to single-core microcapsules having a continuous shell. The shell may consist of natural, semisynthetic or synthetic materials. Natural shell materials are, for example, gum arabic, agar agar, agarose, maltodextrins, alginic acid or salts thereof, e.g. sodium alginate or calcium alginate, fats and fatty acids, cetyl alcohol, collagen, chitosan, lecithins, gelatin, albumin, shellac, polysaccharides such as starch or dextran, sucrose and waxes. Semisynthetic shell materials include chemically modified celluloses, especially cellulose esters and ethers, e.g. cellulose acetate, ethyl cellulose, hydroxypropyl cellulose, hydroxypropyl methylcellulose and carboxymethyl cellulose, and also starch derivatives, especially starch ethers and esters. Synthetic shell materials are, for example, polymers such as polyacrylates, polyamides, polyvinyl alcohol or polyvinylpyrrolidone.

Preferably, the capsules are microcapsules having a water-insoluble wall material, preferably polyurethanes, polyolefins, polyamides, polyesters, polysaccharides, epoxy resins, silicone resins and/or polycondensation products of carbonyl compounds and compounds containing NH groups.

The procedure in microcapsule production as such is well known to those skilled in the art. Suitable processes for microcapsule production are familiar to those skilled in the art and are described, for example, in U.S. Pat. No. 387,052, in U.S. Pat. No. 3,516,941, in U.S. Pat. No. 3,415,758 or else in EP 0026914 A1. The latter describes, for example, microcapsule production by acid-induced condensation of melamine-formaldehyde precondensates and/or the C1-C4-alkyl ethers thereof in water with the hydrophobic material that forms the capsule core dispersed therein, in the presence of a protective colloid.

It is possible with preference to use, for example, melamine-urea-formaldehyde microcapsules or melamine-formaldehyde microcapsules or urea-formaldehyde microcapsules, obtainable, for example, from 3M Corporation or BASF.

Suitable microcapsules are also described, for example, in WO 2001/049817 A2.

The microcapsules are obtainable by processes known in the prior art, the processes of the greatest significance being coacervation and interfacial polymerization. Microcapsules used may be all the surfactant-stable microcapsules supplied on the market, for example the following commercial products (with the shell material stated in brackets in each case): Hallcrest Microcapsules (gelatin, gum arabic), Coletica Thalaspheres (maritime collagen), Lipotec Millicapsules (alginic acid, agar agar), Induchem Unispheres (lactose, microcrystalline cellulose, hydroxypropyl methylcellulose); Unicerin C30 (lactose, microcrystalline cellulose, hydroxypropyl methylcellulose), Kobo Glycospheres (modified starch, fatty acid esters, phospholipids), Softspheres (modified agar agar) and Kuhs Probiol Nanospheres (phospholipids).

Alternatively, it is also possible to use particles which do not have core-shell structure, but in which the active ingredient is distributed in a matrix of a matrix-forming material. Such particles are also referred to as "speckles".

A preferred matrix-forming material is alginate. For production of alginate-based speckles, an aqueous alginate solution also containing the active ingredient(s) to be incorporated is dropletized and then hardened in a precipitation bath containing $Ca^{2+}$ ions or $Al^{3+}$ ions. It may be advantageous for the alginate-based speckles then to be washed with water and then washed in an aqueous solution containing a complexing agent, in order to wash out free $Ca^{2+}$ ions or free $Al^{3+}$ ions which can enter into unwanted interactions with ingredients of the liquid washing and cleaning composition, for example the fatty acid soaps. Subsequently, the alginate-based speckles are washed once more with water in order to remove excess complexing agent. Alternatively, rather than alginate, it is possible to use other matrix-forming materials. Examples of matrix-forming materials include polyethylene glycol, polyvinylpyrrolidone, polymethacrylate, polylysine, poloxamer, polyvinyl alcohol, polyacrylic acid, polyethylene oxide, polyethoxyoxazoline, albumin, gelatin, acacia, chitosan, cellulose, dextran, Ficoll®, starch, hydroxyethyl cellulose, hydroxypropyl cellulose, hydroxypropyl methylcellulose, hyaluronic acid, carboxymethyl cellulose, deacetylated chitosan, dextran sulphate and derivatives of these materials. Matrix formation in the case of these materials is effected, for example, via gelation, polyanion-polycation interactions or polyelectrolyte-metal ion interactions, and is well known in the prior art, just like the production of particles with these matrix-forming materials.

Within the scope allowed by production, the capsules may have any desired shape, but they are preferably approximately spherical.

The diameter thereof along the greatest spatial dimension may, according to the components present in the interior thereof and the use, be between 0.01 nm (not visually perceptible as a capsule) and 1000 µm.

Microcapsules usable with preference as particles, powder or granules which comprise the cleaning and/or detergent ingredients, have mean diameters in the range from 0.1 µm to 100 µm, preferably from 10 µm to 500 µm, more preferred from 80 µm to 100 µm. The shell of the microcapsules that surrounds the core or (filled) cavity has an average thickness in the range between about 75 and 300 nm, preferably between about 80 nm and about 250 nm, especially between about 90 nm and about 200 nm.

Depending on the intended use the capsules for washing and cleaning compositions, in particular detergent compositions, can be produced in all various dimensions, thus the aforementioned sizes for capsules should not limit the capsule dimensions for particles, powder or granules of the washing and cleaning compositions, in particular detergent compositions of the present invention.

Within the capsules, in case they represent particles, powder or granules of the washing and cleaning composition, preferably detergent composition according to the invention, the capsules usually comprise various ingredients, e.g. sensitive, chemically or physically incompatible and volatile components (=active ingredients) of the washing and cleaning composition in a storage- and transport-stable form. Examples of components present within the capsules may be optical brighteners, surfactants, complexing agents, bleaches, bleach activators, dyes, antioxidants, builders, enzymes, and enzyme stabilizers, active antimicrobial ingredients, greying inhibitors, anti-redisposition agents, pH modifiers, electrolytes, foam inhibitors and UV absorbers. In addition, the capsules may contain cationic surfactants, vitamins, proteins, preservatives, washing power enhancers or pearlescent agents. The contents of the capsules may be solids or liquids in the form of solutions or emulsions or suspensions.

The active ingredients are typically released from the capsules during the use of the compositions that comprise them through destruction of the shell or the matrix as a result of mechanical, thermal, chemical or enzymatic action. In a preferred embodiment of the invention, the liquid washing and cleaning compositions contain identical or different capsules in amounts of 0.01% to 10% by weight, especially 0.03% to 5% by weight and exceptionally preferably 0.05% to 2.5% by weight.

Fragrances which have been formed to be microcapsules that fulfil the aforementioned parameters are stabilized particularly efficiently in the dispersion and thus show good results in the context of the invention. Fragrance microcapsules preferably have a have a $d_v(50)$ value from 5 µm to 60 µm, preferably from 10 µm to 50 µm, more preferred from 10 µm to 40 µm and/or a $d_v(90)$ value from 140 µm to 180 µm, preferably 145 µm to 170 µm, more preferably from 150 µm to 160 µm.

In a preferred embodiment the above described perfume capsules are obtained or provided as a slurry containing about 30 wt. % to 99 wt. %, preferably 40 wt. % to 98 wt. %, more preferred 50 wt. % to 95 wt. % water and from 5 wt. % to 60 wt. %, preferably from 20 wt. % to 50 wt. %, most preferably from 30 wt. % to 40 wt. %, of encapsulated fragrances. The encapsulated fragrances have a $d_v(50)$ value from 5 µm to 60 µm, preferably from 10 µm to 50 µm, more preferred from 10 µm to 40 µm and/or a $d_v(90)$ value from 140 µm to 180 µm, preferably 145 µm to 170 µm, more preferably from 150 µm to 160 µm. Normally, the fragrance capsules contain from about 10% to about 95%, more preferably from about 60% to about 85%, by weight of the capsule, of a perfume core. In a second step herein the slurry is sprayed onto particles, powder or granules of a washing and cleaning composition, preferably detergent composition. The particles, powder or granules used to comprise typical washing or cleaning ingredients as described aforementioned.

Thus a further aspect of the present invention is a method for producing perfumed particles, powder or granules, preferably particles, powder or granules for washing and cleaning compositions, more preferred for detergent compositions, comprising the steps of:

I) providing particles, powder or granules, preferably washing and cleaning, more preferred detergent particles, powder or granules, which comprises washing and cleaning, respectively detergent ingredients;

II) obtaining or preparing a dispersion comprising
  A) 0.1 wt. % to 80 wt. %, preferably 1 wt. % to 70 wt. %, more preferred 15 wt. % to 50 wt. % encapsulated fragrances;
  B) optionally 0.001 wt. % to 10 wt. %, preferably 0.01 wt. % to 7 wt. %, more preferred 0.01 wt. % to 2 wt. % viscosity modifiers,
  C) optionally 0.001 wt. % to 80 wt. %, preferably 0.1 wt. % to 70 wt. %, more preferred 15 wt. % to 50 wt. % non-encapsulated fragrances,
  D) 0.001 wt. % to 99 wt. % additives,
  E) 30 wt. % to 99 wt. %, preferably 40 wt. % to 98 wt. %, more preferred 50 wt. % to 95 wt. % water;
  all weight percent of the compounds A) to E) are referred to the total amount of the dispersion and with the proviso that the components add to 100 wt. %;

III) spraying the dispersion step II) onto the particles, powder or granules of step I), wherein the temperature during the spraying is from 15° C. to 120° C., preferably from 35° C. to 90° C., more preferred from 40° C. to 60° C.

In a preferred embodiment of the method of the present invention the capsules of the encapsulated fragrances in the dispersion have a $d_v(50)$ value from 5 µm to 60 µm, preferably from 10 µm to 50 µm, more preferred from 10 µm to 40 µm and/or a $d_v(90)$ value from 140 µm to 180 µm, preferably 145 µm to 170 µm, more preferably from 150 µm to 160 µm and the viscosity of the dispersion which is to be sprayed onto the particles, powder or granules of the washing and cleaning composition, preferably detergent composition is adjusted to 5 mPas to 400 mPas, preferably from 15 mPas to 300 mPas, more preferred 20 mPas to 250 mPas, measured before the dispersion is sprayed onto the particles, powder or granules of step I).

Another object of the present invention is a particulate detergent composition with an angle of repose less than 60°, preferably less than 50°, more preferred less than 45° measured according to DIN ISO 4324. Advantageously, the angle of repose is from 32° to 40°, measured according to DIN ISO 4324.

The particulate detergent composition means a powdery detergent composition and should be understood to be not a liquid composition. Suitable examples for such detergents encompass heavy duty powder detergents, light duty powder detergents, manual dish wash agents, all-purpose cleaners and the like.

In a preferred embodiment the particulate detergent composition of the present invention comprises a plurality of detergent particles wherein the encapsulated fragrances are anchored and thus sprayed to the detergent particles according to the methods as described aforementioned.

Preference is made to a particulate detergent composition according to the invention, wherein in the method for producing perfumed particles, powder or granules, preferably particles, powder or granules for washing and cleaning compositions, more preferred for detergent compositions, comprising the steps of:

I) providing particles, powder or granules, which comprises washing and cleaning, respectively detergent ingredients;

II) obtaining or preparing a dispersion comprising
  A) 0.1 wt. % to 80 wt. %, preferably 1 wt. % to 70 wt. %, more preferred 15 wt. % to 50 wt. % encapsulated fragrances;

B) optionally 0.001 wt. % to 10 wt. %, preferably 0.01 wt. % to 7 wt. %, more preferred 0.01 wt. % to 2 wt. % viscosity modifiers, C) optionally 0.001 wt. % to 80 wt. %, preferably 0.1 wt. % to 70 wt. %, more preferred 15 wt. % to 50 wt. % non-encapsulated fragrances, D) 0.001 wt. % to 99 wt. % additives, E) 30 wt. % to 99 wt. %, preferably 40 wt. % to 98 wt. %, more preferred 50 wt. % to 95 wt. % water;

all weight percent of the compounds A) to E) are referred to the total amount of the dispersion and with the proviso that the components add to 100 wt. %;

III) spraying the dispersion of step II) onto the detergent particles, powder or granules of step I), wherein the temperature during the spraying is from 15° C. to 120° C., preferably from 35° C. to 90° C., more preferred from 40° C. to 60° C.

The dispersion of step II) preferably comprises
i) 30 wt. % to 45 wt. % encapsulated fragrances,
ii) 0.1 wt. % to 0.2 wt. % viscosity modifiers, and
iii) water,
on provision that the compounds add together to 100 wt. %.

In a further embodiment the dispersion of step II) preferably comprises
i) 30 wt. % to 45 wt. % encapsulated fragrances,
ii) 0.1 wt. % to 0.2 wt. % viscosity modifiers,
iii) 15 wt. % to 50 wt. % non-encapsulated fragrances, and
iv) water,
on provision that the compounds add together to 100 wt. %.

In another further embodiment the dispersion of step II) preferably comprises
i) 30 wt. % to 45 wt. % encapsulated fragrances,
ii) 0.1 wt. % to 0.2 wt. % viscosity modifiers,
iii) 15 wt. % to 50 wt. % non-encapsulated fragrances,
iv) 2 wt. % to 30 wt. % additive, and
v) water,
on provision that the compounds add together to 100 wt. %.

A further object is a particulate detergent composition obtainable by the methods as described aforementioned, in particular through the method of producing perfumed particles, powder or granules, preferably particles, powder or granules for washing and cleaning compositions, more preferred for detergent compositions, comprising the steps of:

I) providing particles, powder or granules, which comprises washing and cleaning, respectively detergent ingredients;

II) obtaining or preparing a dispersion comprising;
A) 0.1 wt. % to 80 wt. %, preferably 1 wt. % to 70 wt. %, more preferred 15 wt. % to 50 wt. % encapsulated fragrances;
B) optionally 0.001 wt. % to 10 wt. %, preferably 0.01 wt. % to 7 wt. %, more preferred 0.01 wt. % to 2 wt. % viscosity modifiers,
C) optionally 0.001 wt. % to 80 wt. %, preferably 0.1 wt. % to 70 wt. %, more preferred 15 wt. % to 50 wt. % non-encapsulated fragrances,
D) 0.001 wt. % to 99 wt. % additives,
E) 30 wt. % to 99 wt. %, preferably 40 wt. % to 98 wt. %, more preferred 50 wt. % to 95 wt. % water;

all weight percent of the compounds A) to E) are referred to the total amount of the dispersion and with the proviso that the components add to 100 wt. %;

III) spraying the dispersion step II) onto the detergent composition of step I), wherein the temperature during the spraying is from 15° C. to 120° C., preferably from 35° C. to 90° C., more preferred from 40° C. to 60° C.

The dispersion of step II) preferably comprises
i) 30 wt. % to 45 wt. % encapsulated fragrances,
ii) 0.1 wt. % to 0.2 wt. % viscosity modifiers, and
iii) water,
on provision that the compounds add together to 100 wt. %.

In a further embodiment the dispersion of step II) preferably comprises
i) 30 wt. % to 45 wt. % encapsulated fragrances,
ii) 0.1 wt. % to 0.2 wt. % viscosity modifiers,
iii) 15 wt. % to 50 wt. % non-encapsulated fragrances, and
iv) water,
on provision that the compounds add together to 100 wt. %.

In another further embodiment the dispersion of step II) preferably comprises
i) 30 wt. % to 45 wt. % encapsulated fragrances,
ii) 0.1 wt. % to 0.2 wt. % viscosity modifiers,
iii) 15 wt. % to 50 wt. % non-encapsulated fragrances,
iv) 2 wt. % to 30 wt. % additive, and
v) water,
on provision that the compounds add together to 100 wt. %.

The particulate detergent composition according to the present invention shows the advantage of an angle of repose less than 60°, preferably less than 50°, more preferred less than 45° measured according to DIN ISO 4324.

Therefore in a preferred embodiment the particulate detergent composition according to the present invention preferably shows an angle of repose less than 45°, preferably less than 40°, more preferred less than 30° measured according to DIN ISO 4324. Advantageously, the angle of repose is from 32° to 40°, measured according to DIN ISO 4324.

Preference is made to dispersions of the present invention in which
i) The viscosity is adjusted to a range preferably from 5 mPas to 400 mPas, preferred from 15 mPas to 300 mPas, more preferred 20 mPas to 250 mPas, and
ii) the capsules of the encapsulated fragrances in the dispersion of the present invention have a $d_v(50)$ value from 5 μm to 60 μm, preferably from 10 μm to 50 μm, more preferred from 10 μm to 40 μm and/or a $d_v(90)$ value from 140 μm to 180 μm, preferably 145 μm to 170 μm, more preferably from 150 μm to 160 μm.

Preference is also made to dispersions of the present invention in which
i) the viscosity is adjusted in such a way that the viscosity is preferably in the range from 0.1 Pas to 0.75 Pas, while the shearing stress is in the range from 2.5 tau to 16 tau. Whereas when the shearing stress is lower than 2.5 tau the viscosity is preferably in the range from 0.75 Pas to 3.5 Pas, and
ii) the capsules of the encapsulated fragrances in the dispersion of the present invention have a $d_v(50)$ value from 5 μm to 60 μm, preferably from 10 μm to 50 μm, more preferred from 10 μm to 40 μm and/or a $d_v(90)$ value from 140 μm to 180 μm, preferably 145 μm to 170 μm, more preferably from 150 μm to 160 μm.

Said dispersions show the advantages described above and thus enable a better spraying of such dispersions in a process to produce perfumed particles, powder or granules.

$D_v(50)$ and $D_v(90)$ are determined by using laser diffraction analysis. It can be carried out by using a Masersizer 2000 by Malvern with the following measure parameters. Analysis model: Mie; refractive index of particles: 1,520; refractive Index of dispersant: 1,330; absorption: 0.1; obsuration: 13 to 15%, volume based result model.

$D_v(50)$ and $D_v(90)$ are for the purpose of the invention advantageously specified in the unit μm and are calculated from the accumulated particle distribution curve. $D_v(50)$ means, that 50% of the volume of the particles have a particle size of less or equal than the value of $D_v(50)$. $D_v(90)$ means, that 90% of the volume of the particles have a particle size of less or equal than the value of $D_v(90)$.

EXAMPLES

Example 1

Dispersions A to D

Dispersions A to D have been prepared. The viscosity of the dispersions has been adjusted through the used viscosity modifiers. A1 and A2 are comparative examples. The compositions are shown in Table 1.

TABLE 1

Dispersion A-D and its viscosity (amounts in % b.w.)

| | Dispersion | | | | |
|---|---|---|---|---|---|
| | A1 | A2 | B | C | D |
| P1 | 43.0 | 43.0 | — | — | — |
| P1* | — | — | 45.0 | 45.0 | 35.0 |
| P2 | 0.2 | 0.2 | 0.2 | — | 30.0 |
| viscosity modifier | 0.1 | 0.1 | 0.1 | 0.1 | 2.0 |
| Additive | 10.0 | 10.0 | 10.0 | 10.0 | 15.0 |
| water | | | add 10 100 | | |
| Viscosity [mPas]* | >500 | <5 | 90 | 15 | 380 |

*The determination of the viscosity in the present invention is carried out by using a cone-plate system with 60 mm cone diameter and 2 degree cone angle at a shear stress of 6.4 Pa (=pascal) at a temperature of 23° C. (e.g. with a rheometer Haake RS1).

P1 and P1*: encapsulated fragrance composition. Mean diameter particle size of P1 is 500-600 μm and of P1* is 200-250 μm. The composition is provided in Table 2.

TABLE 2

Composition of P1 and P1*

| Substance | V |
|---|---|
| Rose oxide | 100 |
| Aldehyde C16 | — |
| Agrunitril | 200 |
| Diphenyloxide | 2 |
| Precyclemone B | 260 |
| Allylamylglycolate | 400 |
| 2-Isobutyl-3-methoxy-pyrazine | 8 |
| Cis-4-decenal | 30 |

P2*: non-encapsulated fragrance composition: Composition of P2 is a mixture of free perfume oils consisting of patchouli, blossom oil and petitgrain oil.

Example 2

Stability of the Dispersion A-D

The stability of the dispersions of example 1 has been detected at room temperature 23° C. and at a storage temperature of 40° C. The results are provided in Table 3.

TABLE 3

Stability results of dispersions A-D

| | Dispersion | | | | |
|---|---|---|---|---|---|
| | A1 | A2 | B | C | D |
| Temperature 23° C. | | | | | |
| Time | | | | | |
| 0 | dispersed phases | dispersed phases | dispersed phases | dispersed phases | dispersed phases |
| 1 week | stable | slight | stable | stable separation | stable |
| 2 weeks | stable | separation | stable | slight separation | stable |
| 4 weeks | stable | separation | stable | slight separation | stable |
| Temperature 40° C. | | | | | |
| Time | | | | | |
| 0 | dispersed phases | dispersed phases | dispersed phases | dispersed phases | dispersed phases |
| 1 week | stable | separation | stable | slight separation | stable |
| 2 weeks | stable | separation | stable | slight separation | stable |
| 4 weeks | stable | separation | stable | separation | stable |

Example 3

Application of the Dispersion to Powder Detergent

A fluid-bed rotor granulator (Glatt GPCG3, Glatt GmbH, Binzen, Germany) was filled with 1 kg of unperfumed washing powder (table 4) and fluidized at 1200 rpm (rounds per minute). Dispersions A1 and B of example 1 were sprayed into the washing powder by using an atomizing nozzle with a diameter of 1.2 mm and using an atomizing air pressure of 2 bar. The inlet air temperature was kept at 40° C.

The particle size of the capsules resulting from dispersion B was $dv(50)=28.0$ μm and was measured with a Mastersizer 2000. The $dv(90)$ of the capsules was 156.8 μm.

The angle of repose of the washing powder was analyzed by using the method described in DIN ISO 4324. Afterwards, the washing powder was collected and split into 10 samples by using a sample divider and the perfume content of each divided sample was analyzed.

For the purpose of comparison (example not according to the invention), a capsule dispersion consisting of capsules as used above and water only, was sprayed in the same manner than carried out in the example according to the invention. The results of the perfume content (in weight %) of the washing powder samples are shown in Table 4. Dispersion B is according to the invention, dispersion A1 serves as comparison.

TABLE 4

| | Perfume content | | | | | | | | | | |
|---|---|---|---|---|---|---|---|---|---|---|---|
| Sample | 1 | 2 | 3 | 4 | 5 | 6 | 7 | 8 | 9 | 10 | average |
| B | 0.99 | 0.95 | 0.95 | 0.99 | 0.93 | 0.93 | 0.98 | 0.90 | 1.14 | 1.08 | 0.98 |
| A1 | 1.43 | 0.63 | 0.04 | 0.19 | 0.17 | 1.03 | 0.64 | 1.14 | 0.36 | 0.50 | 0.61 |

The results clearly show that the samples according to the invention have a very consistent perfume content which is high in average over all samples. This is important, as for each load of the washing machine there should be an equal perfume content to give an reliable and equal intensity in smell of the laundry.

The comparative example shows very unsteady perfume contents and is finally low in aver-age over all samples. Therefore each load of a washing machine would result in a different intensity of the smell of the laundry. The composition of the powder detergent is provided in Table 5.

TABLE 5

Composition of the powder detergent

| Composition | E1 | E2 | E3 | E4 | E5 | E6 |
|---|---|---|---|---|---|---|
| Sodium Laureth-1 Sulphate | 12.0 | 8.0 | 8.0 | 4.0 | 4.0 | — |
| Dodecylbenzene sulphonate | — | — | 4.0 | 8.0 | 4.0 | 8.0 |
| Sodium Lauryl Sulphate | — | 4.0 | — | — | 4.0 | 4.0 |
| Coco Fatty Acid, Sodium Salt | 1.0 | 1.0 | 1.0 | 1.0 | 1.0 | 1.0 |
| Coco Glucosides | — | — | — | 7.0 | — | — |
| Laureth-5 | 7.0 | 7.0 | 7.0 | — | 7.0 | 7.0 |
| Zeolite A | 24.0 | 24.0 | 24.0 | 24.0 | 24.0 | 24.0 |
| Sodium silicate, amorphous (modulus 1:2) | 3.0 | 3.0 | 3.0 | 3.0 | 3.0 | 3.0 |
| Sodium carbonate | 12.0 | 12.0 | 12.0 | 12.0 | 12.0 | 12.0 |
| Polymeric polycarboxylate | 5.5 | 5.5 | 5.5 | 5.5 | 5.5 | 5.5 |
| Perborate monohydrate | 16.0 | 16.0 | 16.0 | 16.0 | 16.0 | 16.0 |
| Tetraacetylethylenediamine | 5.5 | 5.5 | 5.5 | 5.5 | 5.5 | 5.5 |
| Carboxymethylcellulose | 0.3 | 0.3 | 0.3 | 0.3 | 0.3 | 0.3 |
| Optical brightener | 0.2 | 0.2 | 0.2 | 0.2 | 0.2 | 0.2 |
| Enzyme granules (protease) | 1.0 | 1.0 | 1.0 | 1.0 | 1.0 | 1.0 |
| NeoScent AA | 0.05 | 0.05 | 0.05 | 0.05 | 0.05 | 0.05 |
| Water | | | ad 100 | | | |

Example 4

Spraying Procedure

The dispersions of example 1 were sprayed according to example 3 onto detergent particles and the spraying step has been observed. The results are shown in Table 6.

TABLE 6

Observations of dispersions A-D in the spraying step

| Spray temperature | Dispersions | | | | |
|---|---|---|---|---|---|
| | A1 | A2 | B | C | D |
| 50° C. | spraying is difficult, nozzles are blocked after a while | Spraying possible | Spraying possible | Spraying possible | Spraying possible |
| 80° C. | Spraying possible, nozzles are blocked after a while | Spraying possible | Spraying possible | Spraying possible | Spraying possible |
| 120° C. | Spraying possible | Spraying possible | Spraying possible | Spraying possible | Spraying possible |

The invention claimed is:

1. A particulate detergent composition with an angle of repose of less than 45° measured according to DIN ISO 4324 comprising a plurality of detergent particles, wherein encapsulated fragrances are anchored to the detergent particles by a process comprising:

I) providing particles, powder or granules, which comprises washing and cleaning, respectively detergent ingredients;

II) obtaining or preparing a dispersion comprising
A) 15 wt. % to 50 wt. % encapsulated fragrances having a mean diameter particle size of from 200 μm to 250 μm;
B) 0.001 wt. % to 10 wt. % viscosity modifiers,
C) 0.001 wt. % to 15 wt. % non-encapsulated fragrances,
D) 0.001 wt. % to 99 wt. % additives, and;
all weight percent of the compounds A) to D) are referred to the total amount of the dispersion, and with the proviso that the components add with water to 100 wt. %; and III) spraying the dispersion of step II) onto the detergent composition of step I), wherein the temperature during the spraying is from 15° C. to 120° C.

2. The particulate detergent composition of claim 1, wherein the viscosity modifiers are selected from the group consisting of water soluble polymers such as polyvinyl pyrrolidone, water soluble cellulose; polyvinyl alcohol; ethylene maleic anhydride copolymer; methyl vinyl ether maleic anhydride copolymer; polyethylene oxides; water soluble polyamide or polyester; copolymers or homopolymers of acrylic acid such as polyacrylic acid, polystyrene acrylic acid copolymers and mixtures thereof.

3. The particulate detergent composition of claim 1, wherein the viscosity of the dispersion is from 5 mPas to 400 mPas.

4. The particulate detergent composition of claim 1, wherein the particle size of the encapsulated fragrances have a $d_v(50)$ value from 5 μm to 60 μm and/or a $d_v(90)$ value from 140 μm to 180 μm.

5. The particulate detergent composition of claim 1, wherein the particle size of the encapsulated fragrances have a dv(50) value from 5 μm to 60 μm and/or a dv(90) value from 140 μm to 180 μm and wherein the viscosity of the dispersion is adjusted to 5 mPas to 400 mPas, measured before the dispersion is sprayed onto the particles, powder or granules of step I).

6. The particulate detergent composition of claim 1, wherein the dispersion in step II) further comprises optical brighteners, surfactants, complexing agents, bleaches, bleach activators, dyes, antioxidants, builders, enzymes, and enzyme stabilizers, active antimicrobial ingredients, greying inhibitors, anti-redisposition agents, pH modifiers, electrolytes, foam inhibitors and UV absorbers, vitamins, proteins, preservatives, pearlescent agents.

7. The composition of claim 1, wherein the dispersion in step II) comprises

A) 30 wt. % to 45 wt. % encapsulated fragrances having a mean diameter particle size of from 200 μm to 250 μm,
B) 0.01 wt. % to 0.2 wt. % viscosity modifiers, and
C) 0.01 wt. % to 0.2 wt. % non-encapsulated fragrances,
on provision that the compounds A) to C) add with additives and water together to 100 wt. %.

* * * * *